(12) United States Patent
Chun et al.

(10) Patent No.: US 8,244,017 B2
(45) Date of Patent: Aug. 14, 2012

(54) CONSTRUCTING THREE DIMENSIONAL IMAGES USING PANORAMIC IMAGES

(76) Inventors: James Jiwen Chun, Raleigh, NC (US); Andrew Youngho Chun, Raleigh, NC (US); Jennifer Miseong Chun, Raleigh, NC (US)

(*) Notice: Subject to any disclaimer, the term of this patent is extended or adjusted under 35 U.S.C. 154(b) by 381 days.

(21) Appl. No.: 12/701,622

(22) Filed: Feb. 8, 2010

(65) Prior Publication Data
US 2011/0194787 A1 Aug. 11, 2011

(51) Int. Cl.
*G06K 9/00* (2006.01)
*G06K 9/64* (2006.01)
(52) U.S. Cl. .......... 382/131; 382/154; 382/285
(58) Field of Classification Search .......... 382/128, 382/131, 154, 285; 378/21–27, 38, 39, 40; 348/36
See application file for complete search history.

(56) References Cited

U.S. PATENT DOCUMENTS

| | | | |
|---|---|---|---|
| 4,630,203 A | 12/1986 | Szirtes | |
| 5,214,686 A | 5/1993 | Webber | |
| 5,841,830 A | 11/1998 | Barni et al. | |
| 6,493,415 B1 | 12/2002 | Arai et al. | |
| 6,587,541 B2 | 7/2003 | Menhardt | |
| 7,317,819 B2 | 1/2008 | Janes | |
| 2009/0322856 A1* | 12/2009 | Duparre | 348/36 |
| 2009/0323891 A1* | 12/2009 | Borghese et al. | 378/20 |

* cited by examiner

*Primary Examiner* — Brian Le
(74) *Attorney, Agent, or Firm* — Ash Tankha; Lipton, Weinberger & Husick

(57) ABSTRACT

A computer implemented method and system for constructing a three dimensional (3D) tomographic image from an object's two dimensional (2D) panoramic image are provided. A first geometrical attribute set in a first coordinate system is assigned to one or more focal troughs. A second geometrical attribute set in a second coordinate system is assigned to the 2D panoramic image. Second geometrical attributes are correlated with first geometrical attributes for reconstructing the 2D panoramic image in multiple dimensions. Multiple defocused elements of the object are determined along the 2D panoramic image's horizontal dimension. A transverse dimension is determined for the reconstructed panoramic image by mapping the defocused elements to a translation along the transverse dimension in the first coordinate system on either side of the center of the focal troughs. The multiple dimensions of the reconstructed panoramic image are transformed into an orthogonal coordinate system to generate the 3D tomographic image.

21 Claims, 9 Drawing Sheets

US 8,244,017 B2

CONSTRUCTING THREE DIMENSIONAL IMAGES USING PANORAMIC IMAGES

BACKGROUND

Dentists have been using panoramic dental images for many years to diagnose dental diseases and disorders. Existing panoramic X-ray imaging machines produce high quality images of the entire dental arch. The entire dentition, the maxillary sinuses, the entire mandible, the temporomandibular joints and other oral facial structures are visible on a single resulting X-ray film. Panoramic imaging machines capture X-ray images along a curved cross-sectional focal plane called a focal trough. The resulting image visible on a panoramic radiograph consists largely of the anatomical structures located within the focal trough. Up until now, panoramic images have been solely presented as two-dimensional images. Although some useful information such as the general shape of the dental structures, and the densities of the teeth and supporting bone along the dental arch can be obtained from the panoramic images, the physical dimensions of the dental structures and the spatial relation of these dental structures are not accurate due to the distortions and limitation of the imaging process.

Presently, three dimensional X-ray images are being recognized by more and more dentists as a valuable tool to diagnose dental diseases. Radiographic techniques, such as, cone beam computer tomography scans are known to generate three dimensional images of anatomical structures with high resolutions. However, certain anatomical structures and certain conditions require patients to be exposed to multiple scans or high doses of radiation to obtain good quality images. According to radiation protection in dentistry, a responsible radiologist keeps the radiation exposure as low as reasonably achievable (ALARA). The basis of radiation protection is that the exposure to the patient should be justifiable such that the total potential diagnostic benefits are greater than the individual detriment radiation exposure might cause.

Therefore, there is a need for a computer implemented method and system that constructs three dimensional images of an object using ordinary two dimensional panoramic images that require low doses of radiation for acquiring single scan images of anatomical structures.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The computer implemented method and system disclosed herein addresses the above stated need for constructing three dimensional images of an object using ordinary two dimensional panoramic images that require low doses of radiation for image acquisition, thereby enhancing diagnostic and radiographic efficiency. An image processing application assigns a set of first geometrical attributes, herein referred to as a "first geometrical attribute set", in a first coordinate system to one or more focal troughs. The focal troughs define curved multidimensional zones relating to predefined focal planes associated with one or more panoramic imaging machines for imaging, for example, dental arches. The first geometrical attribute set represents a vertical dimension, a rotational dimension, and a transverse dimension in the first coordinate system. The image processing application assigns a set of second geometrical attributes, herein referred to as a "second geometrical attribute set", in a second coordinate system to a two dimensional panoramic image of the object. The two dimensional panoramic image is a two dimensional projection of the object developed using the panoramic imaging machines. The second geometrical attribute set represents a vertical dimension and a horizontal dimension in the second coordinate system. As used herein, a "geometrical attribute" refers to a scalar, a vector or a combination of a scalar and a vector, and is used to designate points in an n-dimensional space. The image processing application reconstructs the two dimensional panoramic image in multiple dimensions. The multiple dimensions of the reconstructed panoramic image comprise the vertical dimension of the first geometrical attribute set, the rotational dimension of the first geometrical attribute set, and a transverse dimension. The image processing application reconstructs the two dimensional panoramic image as follows: The image processing application correlates one or more of the second geometrical attributes with one or more of the first geometrical attributes. The vertical dimension represented by the second geometrical attribute set corresponds to the vertical dimension represented by the first geometrical attribute set. The horizontal dimension represented by the second geometrical attribute set corresponds to the rotational dimension represented by the first geometrical attribute set. For each of one or more discrete points on the two dimensional panoramic image, the image processing application determines multiple defocused elements of the object along the horizontal dimension of the two dimensional panoramic image. The image processing application determines the transverse dimension for the reconstructed panoramic image by mapping the defocused elements along the horizontal dimension of the two dimensional panoramic image to a translation along the transverse dimension in the first coordinate system on either side of the center of the focal troughs. The image processing application then transforms the multiple dimensions of the reconstructed panoramic image into an orthogonal coordinate system to generate the three dimensional tomographic image of the object.

In an embodiment, for each of the discrete points on the two dimensional panoramic image, the image processing application also determines multiple defocused elements of the object along the vertical dimension of the two dimensional panoramic image. The image processing application generates the three dimensional tomographic image using the orthogonal coordinate system. The orthogonal coordinate system is, for example, a Cartesian coordinate system.

The image processing application also generates a multi-layered three dimensional image by stacking multiple three dimensional tomographic images with thinner focal troughs. Furthermore, the image processing application generates two dimensional cephalometric images using the three dimensional tomographic image. The image processing application obtains a trajectory of the center of rotation of an electromagnetic radiation source, for example, an X-ray source of the panoramic imaging machines that rotates around the object, in the first coordinate system. The trajectory of the center of rotation of the electromagnetic radiation source achieves the predefined focal planes. The image processing application also obtains a measured speed of rotation of the electromagnetic radiation source around the object and a measured speed of rotation of a rotating image film drum of the panoramic imaging machines.

The generated three dimensional tomographic image can be used in, for example, dental implant treatment planning, imaging of maxillary sinus impacted teeth, third molar nerve, foreign body and other pathologies, analyzing temporomandibular joint functions, and orthodontic treatment planning. For example, orthodontists can use the generated three dimensional images to record and understand the shape of the dental arch, amount of arch space needed to align teeth, and a course of root movement during orthodontic treatment. The computer implemented method and system disclosed herein greatly enhances the diagnostic power, with the same doses of radiation required for acquiring two dimensional images, thereby reducing the risk and radiation exposure to as low as reasonably achievable.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1:
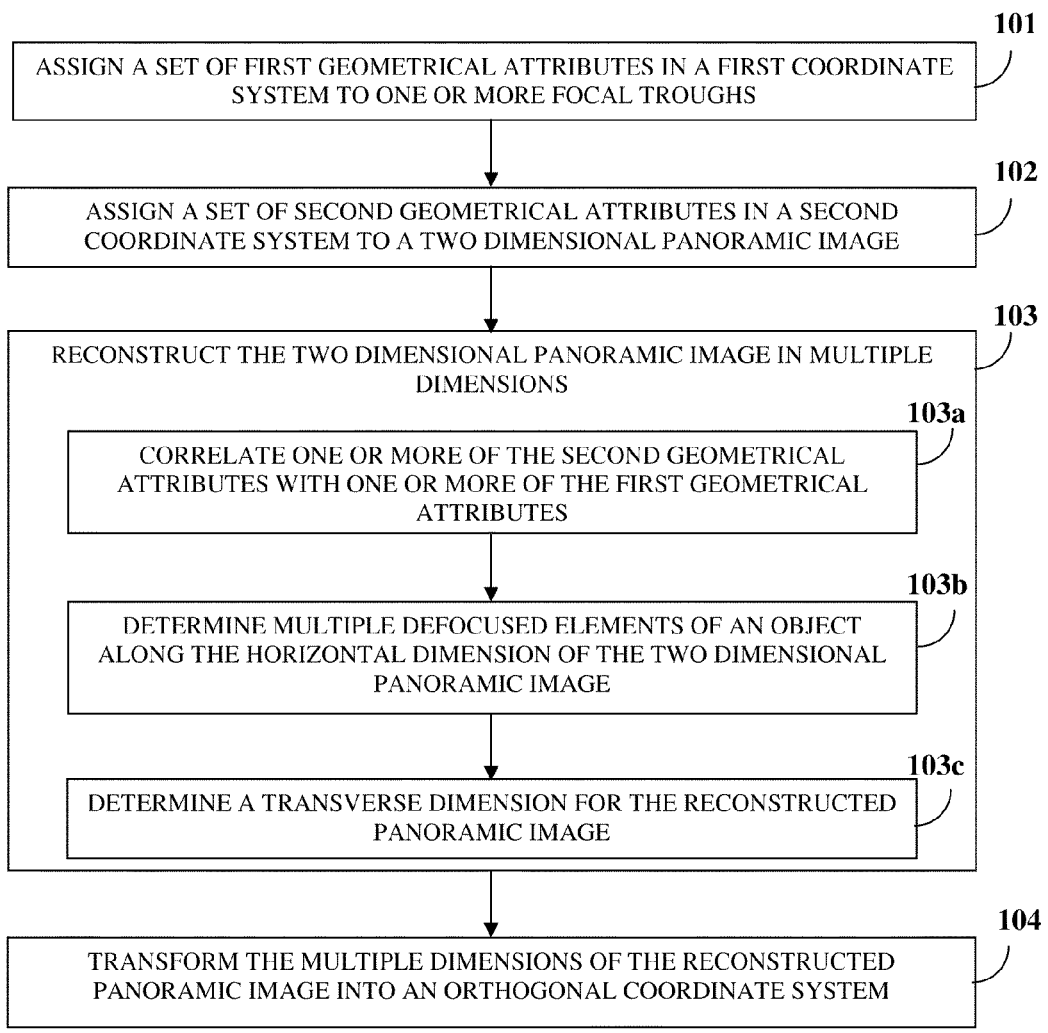
FIG. 1 illustrates a computer implemented method of constructing a three dimensional tomographic image from a two dimensional panoramic image of an object.

FIG. 1 illustrates a computer implemented method of constructing a three dimensional tomographic image from a two dimensional panoramic image of an object, for example, the dental arch of a patient. A set of first geometrical attributes, herein referred to as a "first geometrical attribute set", in a first coordinate system is assigned 101 to one or more focal troughs. As used herein, a focal trough refers to a curved multidimensional zone relating to a predefined focal plane associated with a panoramic imaging machine for imaging the dental arch. The predefined focal plane is also referred to as a focal trough plane. The focal trough of the panoramic imaging machine is a three dimensional curved zone in which images of object structures are reasonably well defined on a panoramic radiograph. The first geometrical attribute set represents a vertical dimension, a rotational dimension, and a transverse dimension in the first coordinate system. As used herein, the first coordinate system refers to a coordinate system that designates discrete points using tuples in a three dimensional space containing the focal trough. Also, as used herein, a dimension refers to a particular direction with respect to a fixed center or origin and/or angular orientation from a fixed direction for measuring and locating discrete points in a two dimensional space and/or a three dimensional space. For example, a vertical dimension is used to measure and locate discrete points along the vertical direction. A set of second geometrical attributes, herein referred to as a "second geometrical attribute set", in a second coordinate system is assigned 102 to the two dimensional panoramic image of the object. The two dimensional panoramic image is a two dimensional projection of the object developed using one or more panoramic imaging machines. The second geometrical attribute set represents a vertical dimension and a horizontal dimension in the second coordinate system. As used herein, the second coordinate system refers to a coordinate system that designates discrete points using tuples on the panoramic image of the object. Also, as used herein, a "geometrical attribute" refers to a scalar, a vector or a combination of a scalar and a vector of points in the first coordinate system and/or the second coordinate system, and is used to designate points in an n-dimensional space.

The two dimensional panoramic image is reconstructed 103 in multiple dimensions. The multiple dimensions of the reconstructed panoramic image comprise the vertical dimension of the first geometrical attribute set, the rotational dimension of the first geometrical attribute set, and a transverse dimension. One or more second geometrical attributes of the second geometrical attribute set are correlated 103a with one or more first geometrical attributes of the first geometrical attribute set. The vertical dimension represented by the second geometrical attribute set corresponds to the vertical dimension represented by the first geometrical attribute set. The horizontal dimension represented by the second geometrical attribute set corresponds to the rotational dimension represented by the first geometrical attribute set. For each of one or more discrete points on the two dimensional panoramic image, multiple defocused elements of the object are determined 103b along the horizontal dimension of the two dimensional panoramic image. A transverse dimension is determined 103c for the reconstructed panoramic image by mapping the defocused elements along the horizontal dimension of the two dimensional panoramic image to a translation along the transverse dimension in the first coordinate system on either or both sides of the center of the focal troughs. The multiple dimensions of the reconstructed panoramic image are transformed 104 into an orthogonal coordinate system to generate the three dimensional tomographic image of the object.

In an embodiment, for each of the discrete points on the two dimensional panoramic image, multiple defocused elements of the object are also determined along the vertical dimension of the two dimensional panoramic image. An image processing application generates the three dimensional tomographic image using the orthogonal coordinate system. The orthogonal coordinate system is, for example, a Cartesian coordinate system.

Figure 2:
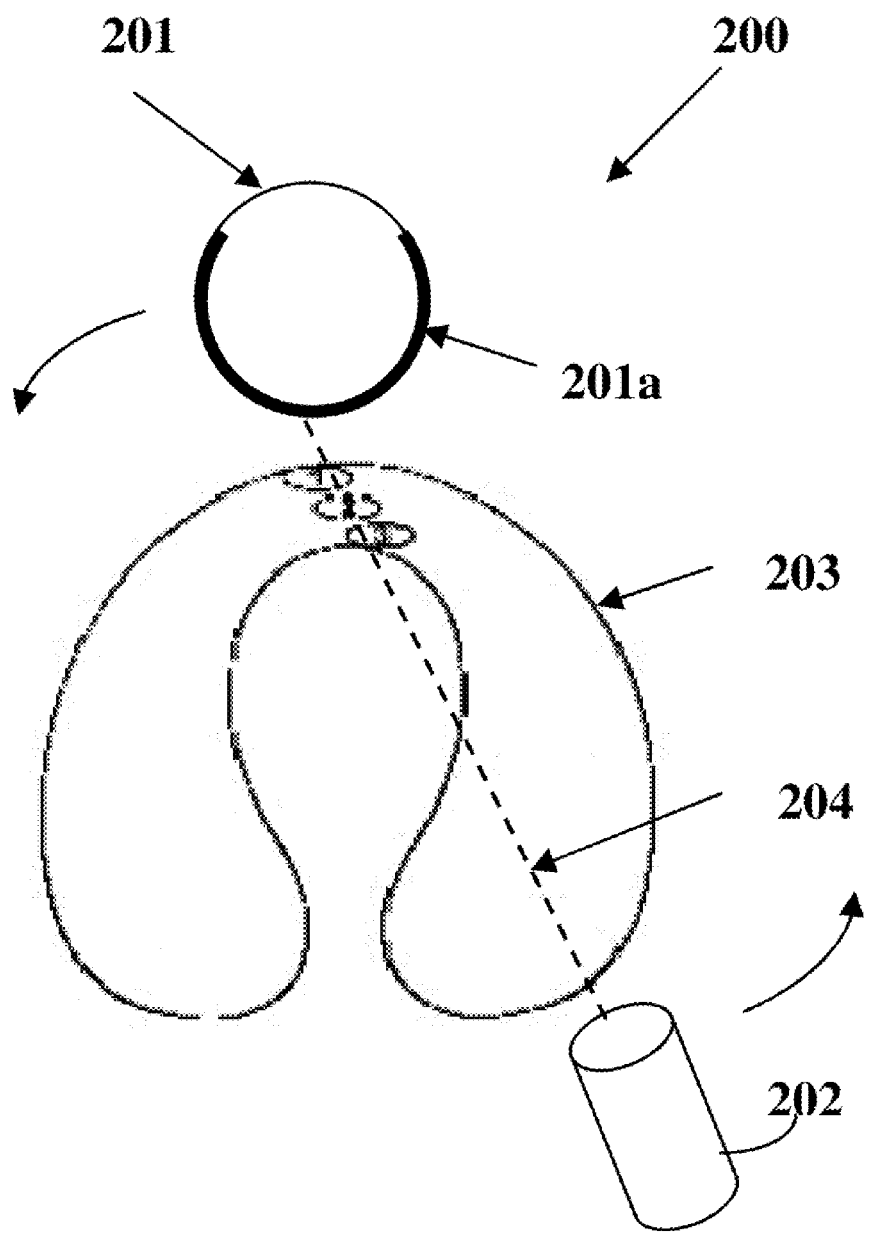
FIG. 2 exemplarily illustrates a logical configuration of a panoramic imaging machine.

FIG. 2 exemplarily illustrates a logical configuration of a panoramic imaging machine 200. The panoramic imaging machine 200 comprises an X-ray tube head 202 and an image film drum 201. The X-ray tube head 202 and the image film drum 201 rotate around an object synchronously and in opposite directions. In a normal arrangement, the X-ray tube head 202 and the film plate 201a are connected through a mechanical linkage 204, for example, a rod whose pivot point coincides with the focal point of the X-ray tube head 202. The image created by the points on the focal plane of the rotating X-ray tube head 202 appear sharper, while the images on other points on either side of the focal plane are blurred or distorted. The panoramic imaging machine 200 captures X-ray images of an object, for example, a dental arch along a curved cross-sectional plane of focus called the focal trough 203. The panoramic images developed are tomographic images of the object along the cross-sectional space defined by the focal trough 203. The focal trough 203 for a panoramic imaging machine 200 is well defined, making it possible to reconstruct the panoramic images in the three dimensional cross-sectional space defined by the focal trough 203 using three dimensional imaging techniques of the computer implemented method disclosed herein. The three dimensional reconstructed image renders an accurate three dimensional layer of the tomographic image of the object. The three dimensional image contains the three dimensional relationship between the teeth, the upper and lower arches and the bone structures, sinus and nasal cavities, both the upper and lower jaws and the temporomandibular joints.

Figure 3A:
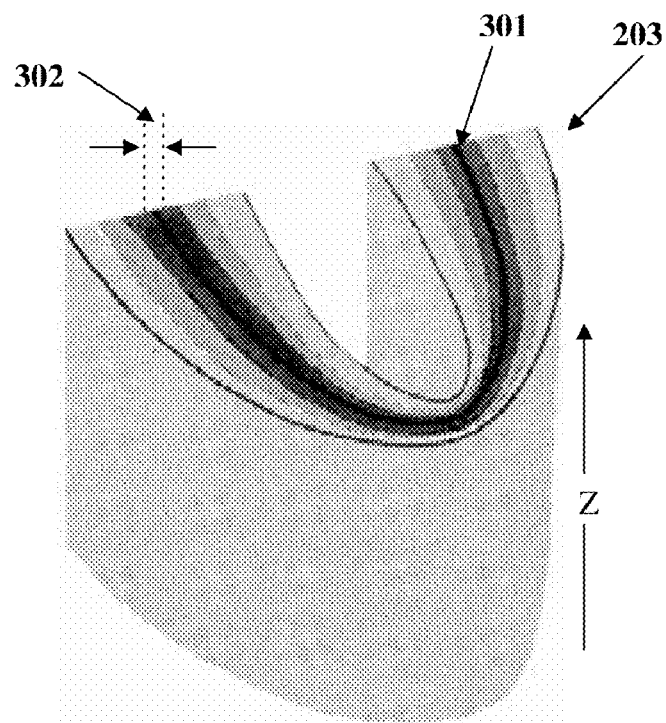
FIG. 3A exemplarily illustrates a focal trough.
Figure 3B:
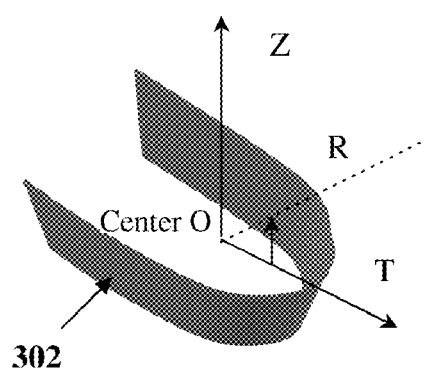
FIG. 3B exemplarily illustrates geometrical attributes of the focal trough in a first coordinate system.

As illustrated in FIG. 2, the panoramic imaging machine 200 uses the principles of tomography in which images are developed by blurring the image of object structures lying superficial and deep to the focal trough plane. The panoramic images are created by rotating both the X-ray tube head 202 and the film plate 201a at the same time. When the exposure begins, the X-ray tube head 202 and the film plate 201a move simultaneously and in opposite directions through the mechanical linkage 204. The image file drum 201 rotates around its axis and the entire image film drum 201 rotates around the center of the focal trough 203. The image of a point on an object that coincides with the focal trough plane 302 or the center plane of the focal trough 203 appears sharper, as illustrated in FIGS. 3A-3B. As the point moves farther from the focal trough plane 302, referred to as defocusing, the blurriness of the image of that point increases. The blurring is also greater if a structure of the object is farther away from the image film, or if the X-ray tube head 202 moves faster. The relation between the speed of the X-ray tube head 202 and the blurring in the developed two dimensional panoramic image is disclosed in the detailed description of FIGS. 4A-4B.

The long axis of the structure relative to the direction of travel for the X-ray tube head 202 can also affect the blurriness. The direction of the travel of the X-ray tube head 202 is parallel to the focal trough 203. If the long axis of the structure is not parallel to the direction of travel, which is the case for most objects, the relative distance of the structure to the focal trough 203 will be different as well. This causes the blurring of the parts of the structure that are located further away from the focal trough 203. The normal arrangement of the panoramic imaging machine 200 is modified for imaging the dental arch, since the dental arch does not define a true arc in a perfect circle. Accordingly, multiple centers of rotation are necessary to maintain the dental arch in the focal trough 203 as the panoramic imaging machine 200 rotates around the patient. The trajectory of the center of rotation of the X-ray tube head 202 for imaging a curved dental arch is predefined such that the X-ray beam successively irradiates structures of the dental arch substantially normal to the dental arch.

The created two-dimensional panoramic image contains distortions due to unequal vertical and horizontal magnification or reduction, superimposition due to overlapping of tooth structures, and loss of image sharpness in the imaging process. The structures recorded on the panoramic image are the two dimensional projections of the structures that have relatively high radio opacity and are within or close to the focal trough 203. If a structure of the object lies on the focal trough 203, the image of the structure will have the least blurriness. If the structure lies away from the focal trough 203, the blurring of the image of the structure is greater.

The degree of blurriness of a structure is a measure of the distance of the structure away from the focal trough 203. Since the long axis of the object may not lie in the same direction as the vertical axis (Z) of the focal trough 203, the blurriness varies along the vertical axis (Z). Hence, the structures of the object on the panoramic images can be characterized by their blurriness, which also indicates the distances of the structures away from the focal trough 203, as a function of their location on the vertical axis. Information regarding distance of the structures away from the focal trough 203 assists in a more accurate approximation of the three dimensional tomography of the object.

The computer implemented method disclosed herein can be divided into three stages, for example, image detection, image reconstruction, and image display. Image detection involves the study and characterization of the focal trough 203 for different types of panoramic imaging machines 200 and numerically constructing the focal trough 203 in the first coordinate system. FIG. 3A exemplarily illustrates a focal trough 203, showing a contour line 301. The image of the points lying on the contour line 301 has the least blurriness. FIG. 3B exemplarily illustrates the geometrical attributes of the focal trough 203 in the first coordinate system. Geometrical attributes representing the vertical dimension (Z), the rotational dimension (R) with the center "O" and the transverse dimension (T) are assigned to the focal trough 203. The rotational center of the X-ray tube head 202 shifts along one or more predefined trajectories. Information such as the centers of the rotation of the image film drum 201, the diameter of the image film drum 201, the rotational axis and the rotational velocity of the image film drum 201, the rotational axis and the rotational velocity of the X-ray tube head 202, the length of rotational arm of the X-ray tube head 202, the trajectories of the center of rotation of the X-ray tube head 202, and other important parameters is collected according to the type of the panoramic imaging machine 200, and then transformed into the first coordinates system with Z, R, T, O coordinates as illustrated in FIG. 3B. The focal trough 203 of the panoramic imaging machine 200 can be quantitatively defined by a function $F(Z, R, T, O)$ in the first coordinate system. This quantitative data is used to establish the coordinates for the three dimensional reconstruction of the two dimensional panoramic image. Typically, the rotational velocity of the image film drum 201 is about 1.7 mm/s and the thickness of the focal trough 203 is about 10 mm. A higher relative speed between the X-ray tube head 202 and the image film drum 201 results in a thinner focal trough 203. As disclosed below, multiple tomographic reproductions of the focal trough 203 can be stacked in order to construct multilayered three dimensional images.

Figure 4A:
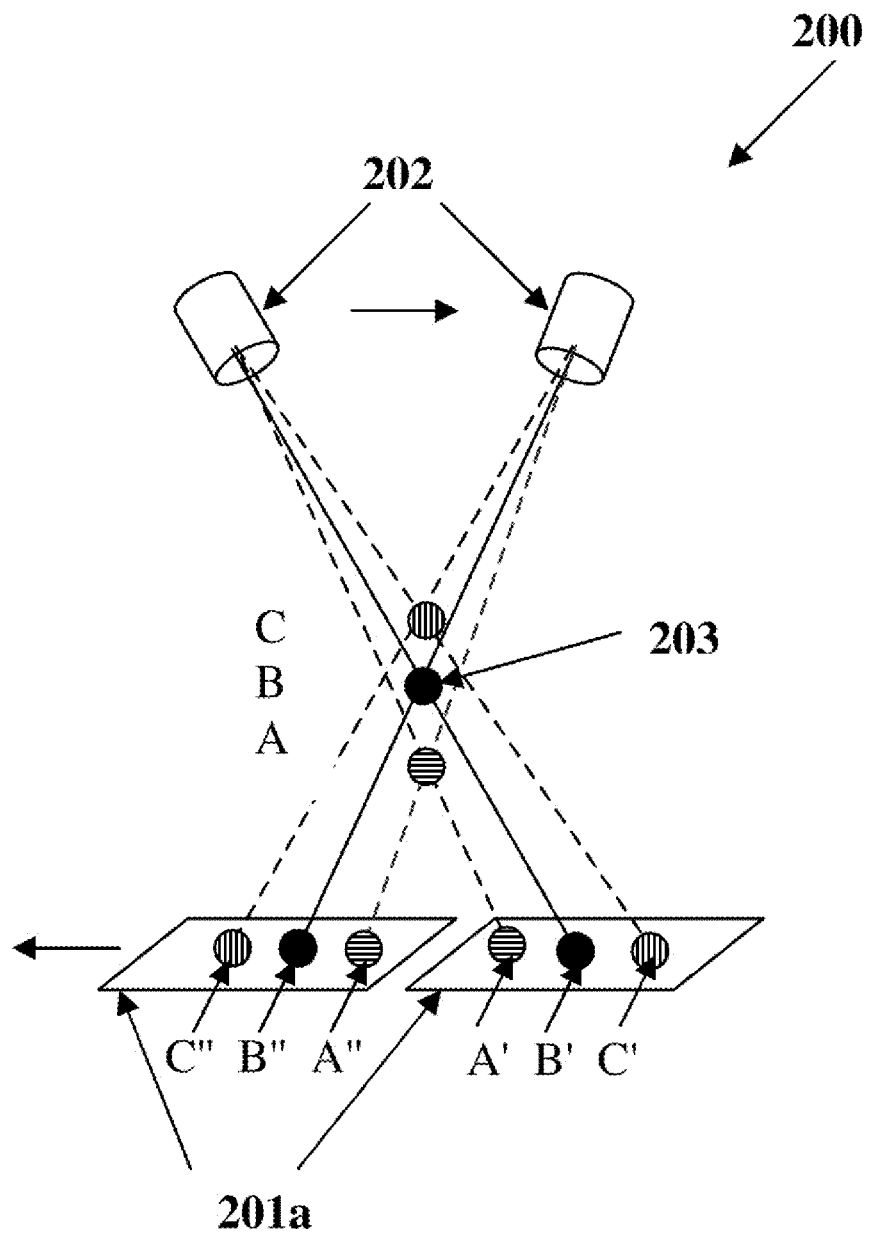
FIG. 4A exemplarily illustrates the geometric principle in radiography showing points transverse to the focal trough.

FIG. 4A exemplarily illustrates the geometric principle in radiography showing points transverse to the focal trough 203. As the X-ray tube head 202 and the film plate 201a move simultaneously, the projected image of the object at point "C" moves forwards on the film plate 201a, while the image of the object at "A" moves backwards. As a result, the images of the object at these two points are blurred during the movement. The greater the distances between points "A" and "B" and points "C" and "B" on the object, the longer is the resulting blurring distances A'A" and C'C" on the projected image, respectively. Also, a higher speed of the X-ray tube head 202 relative to the image film drum 201 results in longer blurring distances A'A" and C'C". In a first order approximation, the equation of motion is of constant speed, and the blurriness of a point is proportional to the distance of the point away from the center of the focal trough 203, and the relative speed of the X-ray tube head 202 and the image film drum 201. On the other hand, the projected image for the object at point "B" remains fixed at the same relative location on the film plate 201a during the movement of the X-ray tube head 202, retaining its sharpness. The curved plane within which point "B" of the object resides is the focal trough plane 302. Given the geometry of the X-ray tube head 202 and the film plate 201a, and the speed of their relative motion, the exact location of the focal trough plane F(Zi, Rj, Tl, O) 302 can be numerically characterized for each type of panoramic imaging machine 200. This function F(Zi, Rj, Tl, O) resembles the function of the contour line 301 illustrated in FIG. 3A. F(Zi, Rj, Tl, O) is a function of distribution that reflects the blurriness of the panoramic image as a function of Zi, Rj, Tl, O, with values ranging from one to zero, where "one" indicates the least blurring, and "zero" indicates complete blurring. F(Zi, Rj, Tl, O) on the contour line 301 has a value of 1 and corresponds to the points on the focal trough 203. However, the points located away from the focal trough plane 302 correspond to the lighter shades on the projected image, and their values decrease dramatically. Indices i, j, and l in the function F(Zi, Rj, Tl, O) are the discrete points along the focal trough 203 from the starting point to the end point. "O" is the location of the center of rotation at any instance. The discrete points are chosen to account for the necessary set of points to construct a three dimensional image. F(Zi, Rj, Tl, O) has a bell shaped curve across the transverse dimension (T) with the peak at the contour line 301 as illustrated in FIG. 4B.

Figure 4B:
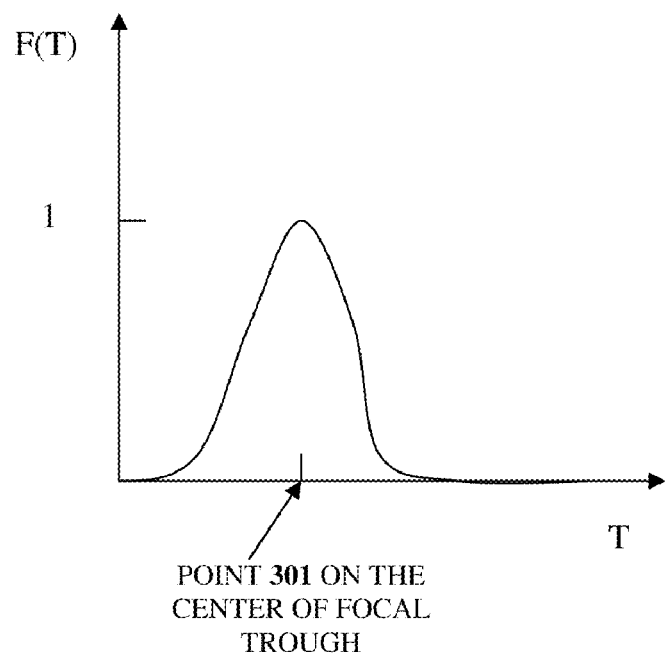
FIG. 4B exemplarily illustrates a distribution curve showing the variation of blurriness along a transverse dimension of the focal trough.

FIG. 4B exemplarily illustrates a distribution curve showing the variation of blurriness along a transverse direction (T) of the focal trough 203. A wider bell shaped curve corresponds to a lower total blurriness. As illustrated in FIG. 4B, the bell shaped curve becomes narrower when the rotational speed increases and consequently when the blurriness increases, from which it can be inferred that a faster relative speed between the X-ray tube head 202 and the image film drum 201 leads to a narrower focal trough 203. The resulting blurring manifests in the blurring of the panoramic image along the horizontal dimension (X). As illustrated in FIG. 4A, the relative rotation between the X-ray tube head 202 and the film plate 201a of the points of C and A, which are positioned away from the focal center B, results in the blurred image of point C as C'C" and point A as A'A" in the horizontal dimension (X) on the film plate 201a.

Figure 5:
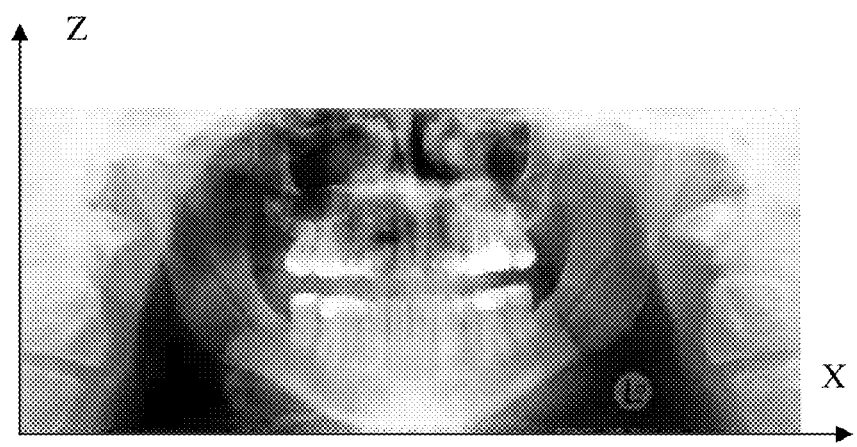
FIG. 5 exemplarily illustrates a panoramic image of a dental arch in a second coordinate system.

Image reconstruction involves the reconstruction of the two dimensional panoramic image data into three dimensional image data. Most panoramic images recorded are usually bitmap data files. Geometrical attributes representing the horizontal dimension (X) and the vertical dimension (Z) from the second coordinate system are assigned to the panoramic image, as illustrated in FIG. 5. FIG. 5 exemplarily illustrates a panoramic image of a dental arch in the second coordinate system. The bitmap data of the panoramic image are converted into numeric data in terms of the X and Y coordinates in the second coordinate system, represented by the tuple P(Zm, Xn).

Figure 6:
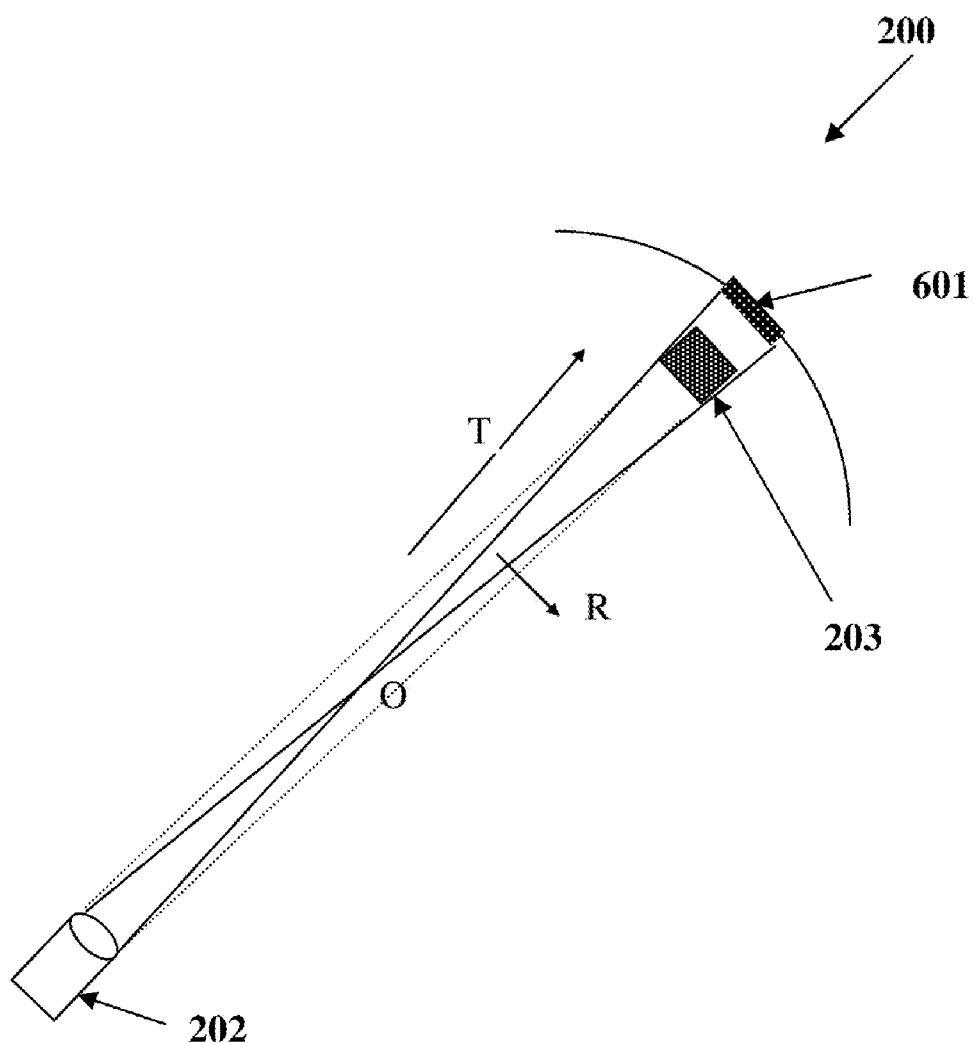
FIG. 6 exemplarily illustrates a geometrical relationship between an X-ray tube head, the focal trough, and a panoramic film plane of a panoramic imaging machine in a first coordinate space.

FIG. 6 exemplarily illustrates a geometrical relationship between the X-ray tube head 202, the focal trough 203 and a panoramic film plane 601 of the panoramic imaging machine 200 in a first coordinate space. The horizontal dimension "X" of the panoramic film plane 601 corresponds to the rotational dimension "R" on the focal trough 203. "Z" is the common vertical axis on the focal trough 203 and the panoramic film plane 601. Thus, the X and Z dimensional data, for example, the discrete values of X and Z on the panoramic film plane P(Zm, Xn) 601 can be readily correlated with the R and Z dimensional data, for example, the discrete values of R and Z of the focal trough plane F(Zi, Rj, Tl, O) 302. The correlation between X and Z dimensional data on the panoramic film plane P(Zm, Xn) 601 and the R and Z dimensional data of the focal trough plane F(Zi, Rj, Tl, O) 302, respectively, is represented by equation 1 as follows:

$$I(Zi, Rj, Tl, O) = F(Zi, Rj, Tl, O) * P(Zm, Xn) \quad \text{(Equation 1)}$$

The resulting reconstructed image data given by I(Zi, Rj, Tl, O) has distortions and blurriness due structures that are distant from the focal trough 203. The reasons for blurriness need to be investigated and properly processed to restore the original image. The distortions and blurriness in the panoramic images occur due to several factors. For example, a penumbra occurs from the size of the focal spot that resulted in non-sharpness near the edge of the panoramic image.

As disclosed in the detailed description of FIGS. 4A-4B, the blurriness along the horizontal dimension (X) on the panoramic image P(Zm, Xn) may occur due to the relative rotational motion between the image film drum 201 and the X-ray tube head 202. The rapid rotational motion results in blurry movement of the image data along the horizontal dimension (X) as illustrated in FIGS. 4A and 5. The natural variation of the data from the object structure is replaced by the prolonged repetition of the data superimposed over time. The patterns of this blurring reflect the relative rotational speed and the distance of the structures away from the focal trough 203, among other factors. Referring to FIG. 4A, the blurriness or defocusing of point C'-C" on the panoramic image is proportional to "BC", the distance between point "C" on the object and point "B" in the focal trough 203. The length of this blurring C'-C" is a function of the relative speed of the rotation and the distance "BC" of point "C" away from the focal trough 203. Since the relative rotational speed between the X-ray tube head 202 and the image film drum 201 is well defined, the length of the repetition determines the distance of the structure at point "C" from the center of the focal trough 203. The length of the blurring quantified or measured in terms of discrete values along the horizontal dimension (X), referred to as a set of defocused elements, is mapped to the transverse dimension (T) represented in the first coordinate system with respect to a discrete point "B" on the center of the focal trough 203. This mapping of the length of blurring to a length along the transverse dimension (T) is repeated for other sets of defocused elements to construct the transverse dimension (T) with respect to other discrete points along center of the focal trough 203. The original image of the structure at point "C" is recreated by identifying the center of the repetition, while the distance of the object structure relative to the focal trough 203 is characterized to obtain an approximation of the three dimensional tomography of the object. The panoramic image data reconstructed in three dimensions, namely, the horizontal dimension (Zi), the rotational dimension (Rj) and the transverse dimension (Tl) provides the image data I(Zi, Rj, Tl, O) in the three dimensional space around the focal trough 203. I(Zi, Rj, Tl, O) resembles the actual physical dimensions of the real object. This set of image data constitutes a narrow band of structures around the focal trough plane 302.

Figure 7:
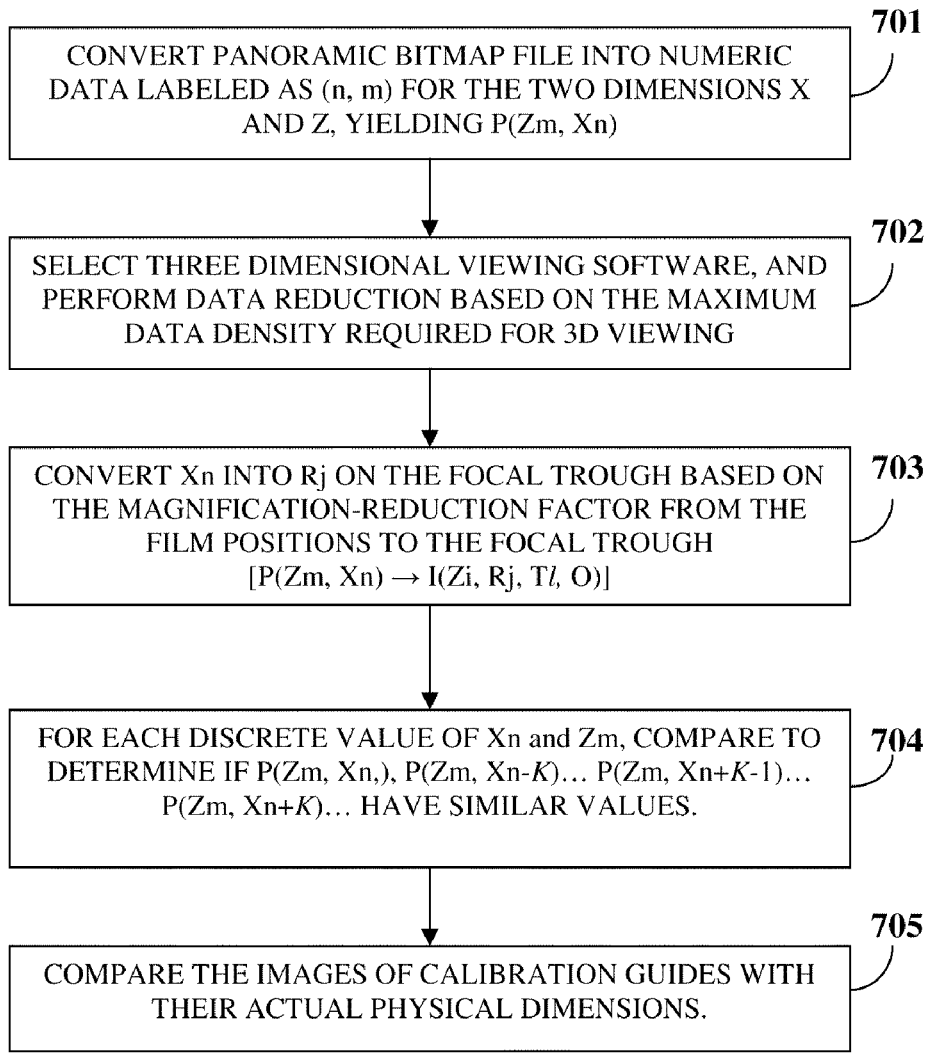
FIG. 7 exemplarily illustrates a process flow diagram comprising the steps for reconstructing the panoramic image.

FIG. 7 exemplarily illustrates a process flow diagram for reconstructing the panoramic image in three dimensions. A panoramic bitmap image file is converted 701 into numeric data labeled as (n, m) for the two dimensions X and Z, yielding P(Zm,Xn). A three dimensional image processing/viewing application is selected 702. Data reduction is performed based on the maximum data density required for three dimensional (3D) viewing. The coordinates Xn are converted 703 into the coordinates Rj on the focal trough 203 based on equation 1 from the positions on the film image to the focal trough 203. This conversion is given by P(Zm, Xn)→I(Zi, Rj, Tl, O).

In order to reconstruct the blurriness in the panoramic image, for each discrete value of Xn and Zm, a series of defocused elements are determined by comparing 704 to check whether the elements P(Zm, Xn), P(Zm, Xn−k), . . . P(Zm, Xn+k−1), . . . P(Zm, Xn+k), . . . have same values within the noise level, where k is the range index for this series of similar values. The center P(Zm, Xn) of this series of defocused elements is identified to correct the blurriness, that is, to obtain the correct value for I(Zi, Rj, Tl, O), where Tl, the translation along the transverse dimension is estimated based on the rotational speeds and the length of blurriness k. When the blurriness in the panoramic image is reconstructed for each discrete value of Xn and Zm, by mapping the length of the blurriness to a length along the transverse dimension (Tl), the resulting transverse dimensional data establishes one or more new planes on either side of the focal trough plane 302 that can be defined in the Zi and Rj coordinates. A new three dimensional data I(Zi, Rj, Tl, O) is thus generated.

In order to ensure the accuracy of the reconstructed image, aluminum calibration guides can be used to calibrate the relative size and location of the panoramic images along the focal trough 203. These calibration guides are embedded in, for example, a bite guide. Patients are instructed to hold the bite guide between their teeth during the imaging process. Regular shaped objects such a triangular cylinder aluminum rod, circular cylinder aluminum rod, etc. are positioned inside a biting guide between upper and lower teeth. These aluminum rods are semi translucent to X-rays, and hence appear as shadows over the panoramic image. The images of the calibration guides given, for example, by $I_{guide}(Zi, Rj, Tl, O)$ are compared 705 with their actual physical dimensions. If discrepancies are detected in these images, further investigations are performed to correct these discrepancies. The calibration guides have well-defined radio densities, and hence can be subtracted from the developed image to recover the intended images. The calibration guides also have well-defined radiographic optical density, shape and locations that can be used to calibrate the image density of the structures of the object and the distance of the structures from the focal through.

Among the initial data, for example, centers of the rotation of the image film drum 201, the relative rotational speed of the image film drum 201 and the X-ray tube head 202, etc., collected from the panoramic imaging machine 200, the data that can be altered by mechanical or human error while acquiring the panoramic image, is the relative rotational speed of the image film drum 201 and the X-ray tube head 202. Thus, special calibration guides can be designed to regain the accuracy of the initial data. Aluminum balls of a small diameter of about 0.5 mm are positioned at various precise distances, for example, 1-5 mm away from a center line of the dental arch, and their images $I_{guide}(Zi, Rj, Tl, O)$ are analyzed. Although the center line of the dental arch can be arbitrary, the relative distances of these calibration balls from the center are precise. These distances on the image are compared to their actual values. If discrepancies between the image and the actual values are found, corrections to the entire image data are made to ensure the accuracy of I(Zi, Rj, Tl, O).

Image display involves the selection and configuration of application software for rendering the three dimensional images. A typical three dimensional image processing/viewing application requires substantially less discrete data points than that required in the panoramic image. Data reduction is performed either at this stage or in the previous stage where the panoramic image data is reconstructed. The three dimensional image processing/viewing application selected allows a viewer to freely rotate and enlarge the object. The reconstructed image data I(Zi, Rj, Tl, O) are transformed or converted from data in X-R-T-O space into the data in X-Y-Z Cartesian coordinates, to obtain V(Zi, Xj, Yl) in the Cartesian coordinate space. In the Cartesian coordinate space, a center of origin along the mid-line is selected as the common origin. The converted data V(Zi, Xj, Yl) are imported into the image processing/viewing application for generating the three dimensional tomographic image of the object. The image processing application incorporates sophisticated algorithms to generate a three dimensional (3D) volumetric data set. The image processing application incorporates basic visual enhancement features, for example, zoom or magnification, window/level, the capability to add annotation, etc. The image processing application also features cursor driven measurement algorithms that provide the viewer or clinician with an interactive capability for real-time dimensional assessment of the generated tomographic image.

In the case of orthodontic diagnosis, most of the important dental and skeletal anatomical features related to the cephalometric landmarks are located near the focal trough 203. Cephalometric analysis is performed for understanding the dental and skeletal development of a patient. Traditionally, separate cephalometric equipment is required to obtain the cephalometric data. In an embodiment of the computer implemented method disclosed herein, the three dimensional tomographic image data obtained from the panoramic images can also be projected into a two dimensional cephalometric X-ray image for enabling cephalometric analysis of the dental arch.

The three dimensional tomographic image also comprises the three dimensional relation of the temporomandibular joint complex. Multiple three dimensional images can be produced with different bite positions. In this case, the patients are instructed to bite a series of occlusal guides in particular inter-occlusal positions. These three dimensional images can be animated into a three dimensional record of the joint movement. Abnormalities associated with the jaw movement, for example, the temporomandibular joint disorder can be diagnosed from these records.

In an embodiment, a faster relative rotation of the X-ray tube head 202 and the image film drum 201 produces a thinner focal trough plane 302. Multiple tomographic image layers of thinner focal trough 203 can be stacked together to produce a multi-layered three dimensional image. This multi-layered three dimensional image comprises comprehensive information in the transverse dimension (T), which is useful in implant treatment.

Figure 8:
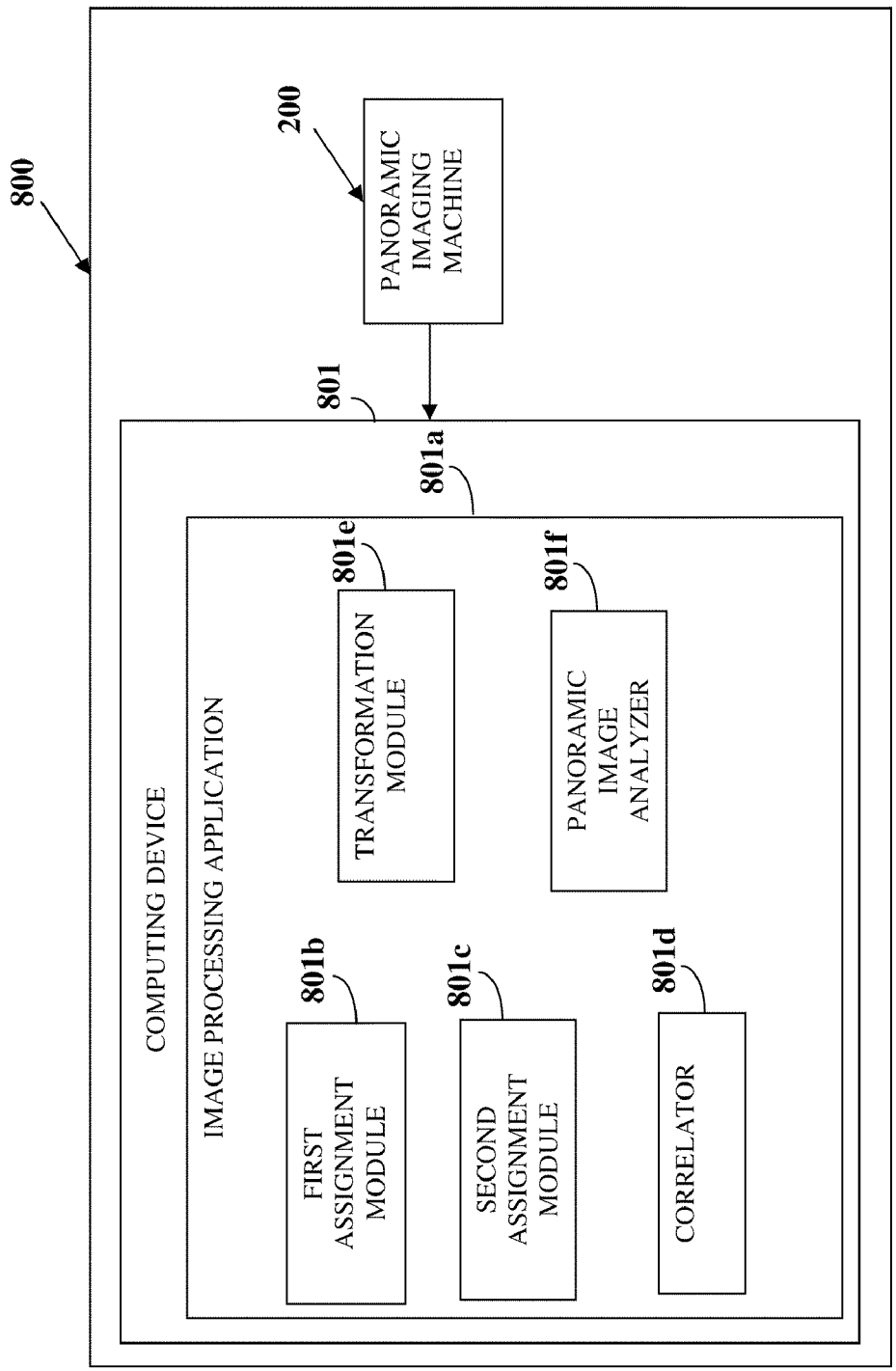
FIG. 8 exemplarily illustrates a computer implemented system for constructing a three dimensional tomographic image from a two dimensional panoramic image of an object.

FIG. 8 exemplarily illustrates a computer implemented system 800 for constructing a three dimensional tomographic image from a two dimensional panoramic image of an object. The two dimensional panoramic image is a two dimensional projection of the object developed using a panoramic imaging machine 200. The computer implemented system 800 disclosed herein comprises one or more panoramic imaging machines 200 having predefined focal trough planes 302, an image processing application 801a provided on a computing device 801, and specific modules that process the data and render a three dimensional view of the object structures, for example, dental structures.

The image processing application 801a on the computing device 801 comprises a first assignment module 801b, a second assignment module 801c, a correlator 801d, a panoramic image analyzer 801f, and a transformation module 801e. The first assignment module 801b assigns a first geometrical attribute set in a first coordinate system to one or more focal troughs 203. The focal troughs 203 define curved multidimensional zones relating to predefined focal trough planes 302 associated with one or more panoramic imaging machines 200. The first geometrical attribute set represents a vertical dimension, a rotational dimension, and a transverse dimension in the first coordinate system. The second assignment module 801c assigns a second geometrical attribute set in a second coordinate system to the two dimensional panoramic image of the object. The second geometrical attribute set represents a vertical dimension and a horizontal dimension in the second coordinate system. The correlator 801d correlates one or more second geometrical attributes with one or more first geometrical attributes for reconstructing the panoramic image in multiple dimensions. The multiple dimensions of the reconstructed panoramic image comprise the vertical dimension represented by the first geometrical attribute set, the rotational dimension of the first geometrical attribute set, and a transverse dimension. The vertical dimension of the second geometrical attribute set corresponds to the vertical dimension of the first geometrical attribute set. The horizontal dimension of the second geometrical attribute set corresponds to the rotational dimension of the first geometrical attribute set.

The panoramic image analyzer 801f determines, for each of one or more discrete points on the two dimensional panoramic image, multiple defocused elements of the object along the horizontal dimension of the two dimensional panoramic image. The panoramic image analyzer 801f determines the transverse dimension for the reconstructed panoramic image by mapping the defocused elements along the horizontal dimension to a translation along the transverse dimension in the first coordinate system on either side of the center of the focal troughs 203. The transformation module 801e transforms the multiple dimensions of the reconstructed panoramic image into an orthogonal coordinate system to generate the three dimensional tomographic image of the object. The image processing application 801a generates the three dimensional tomographic image using an orthogonal coordinate system.

In an embodiment, instead of manually feeding the information about the panoramic imaging machine 200 into the computing device 801, the computer implemented system 800 can include a specially configured panoramic imaging machine 200 interfaced with the computing device 801 such that the computing device 801 can automatically collect configurable information, for example, the centers of rotation of the image film drum 201, the diameter of the image film drum 201, the rotational axis and the rotational velocity of the image film drum 201, the rotational axis and the rotational velocity of the X-ray tube head 202, the length of rotational arm of the X-ray tube head 202, the trajectories of center of rotation of the X-ray tube head 202, etc. from the panoramic imaging machine 200.

In an embodiment, the panoramic image analyzer 801f also determines multiple defocused elements of the object along the vertical dimension of the two dimensional panoramic image for each of the discrete points on the two dimensional panoramic image. The image processing application 801a generates a multi-layered three dimensional image by stacking multiple three dimensional tomographic images with thinner focal troughs 203. The image processing application 801a also generates two dimensional cephalometric images using the generated three dimensional tomographic image. In an embodiment, the first assignment module 801b obtains a trajectory of the center of rotation of an electromagnetic radiation source, for example, the X-ray source of the panoramic imaging machine 200 that rotates around the object in the first coordinate system. The trajectory of the center of rotation of the X-ray source achieves the predefined focal trough plane 302. The first assignment module 801b also obtains a measured speed of rotation of the X-ray source around the object and a measured speed of rotation of the rotating image film drum 201 of the panoramic imaging machine 200.

In an embodiment, the computer applications and programs, for example, the image processing application 801a may be operated in a remote location. The image files, for example, the bitmap files can be electronically transmitted to a remote computing device, where web-based viewable images, for example, PNG files are returned to an online user. Information regarding the panoramic imaging machines 200 and calibration guides are required or made available at the remote computing device for an accurate construction of the three dimensional tomographic image.

Figure 9:
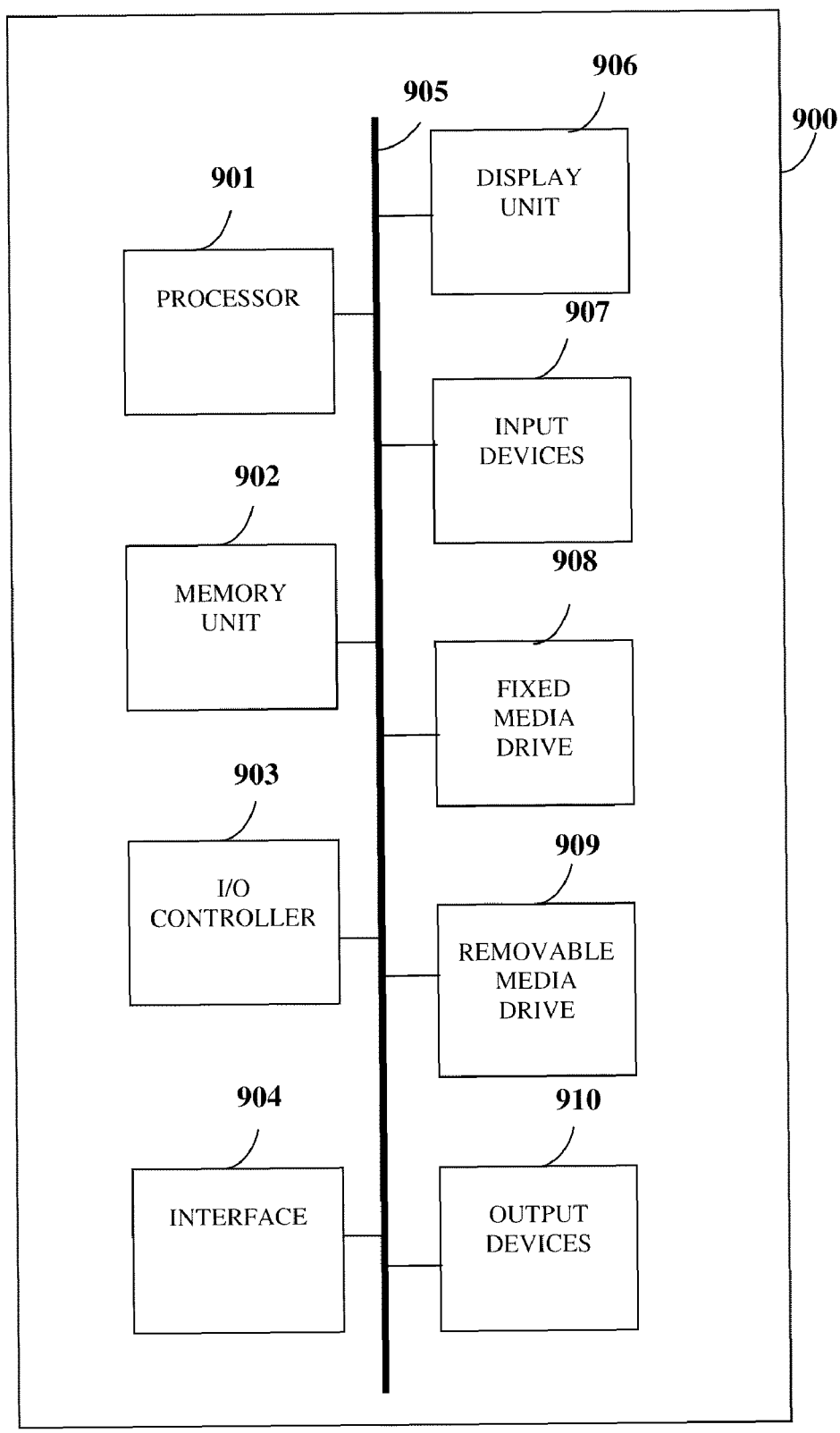
FIG. 9 exemplarily illustrates the architecture of a computer system used for constructing a three dimensional tomographic image from a two dimensional panoramic image of an object.

FIG. 9 exemplarily illustrates the architecture of a computer system 900 used for constructing a three dimensional tomographic image from a two dimensional panoramic image of an object. The computer system 900 comprises a processor 901, a memory unit 902 for storing programs and data, an input/output (I/O) controller 903, and a display unit 906 communicating via a data bus 905. The memory unit 902 comprises a random access memory (RAM) and a read only memory (ROM). The computer system 900 comprises one or more input devices 907, for example, a keyboard such as an alphanumeric keyboard, a mouse, a joystick, etc. The input/output (I/O) controller 903 controls the input and output actions performed by a user. The computer system 900 communicates with other computer systems through an interface 904, comprising, for example, a Bluetooth™ interface, an infrared (IR) interface, a WiFi interface, a universal serial bus interface (USB), a local area network (LAN) or wide area network (WAN) interface, etc.

The processor 901 is an electronic circuit that can execute computer programs. The memory unit 902 is used for storing programs, applications, and data. For example, the image processing application 801a is stored on the memory unit 902 of the computer system 900. The memory unit 902 is, for example, a random access memory (RAM) or another type of dynamic storage device that stores information and instructions for execution by processor 901. The memory unit 902 also stores temporary variables and other intermediate information used during execution of the instructions by the processor 901. The computer system 900 further comprises a read only memory (ROM) or another type of static storage device that stores static information and instructions for the processor 901. The I/O controller 903 controls the input and output actions performed by the user. The data bus 905 permits communication between the modules, for example, 801b, 801c, 801d, 801e, and 801f of the computer implemented system 800 disclosed herein.

Computer applications and programs are used for operating the computer system 900. The programs are loaded onto the fixed media drive 908 and into the memory unit 902 of the computer system 900 via the removable media drive 909. In an embodiment, the computer applications and programs may be loaded directly through the network. Computer applications and programs are executed by double clicking a related icon displayed on the display unit 906 using one of the input devices 907. The user interacts with the computer system 900 using a graphical user interface (GUI) of the display unit 906.

The computer system 900 employs an operating system for performing multiple tasks. The operating system manages execution of, for example, the image processing application 801a provided on the computer system 900. The operating system further manages security of the computer system 900, peripheral devices connected to the computer system 900, and network connections. The operating system employed on the computer system 900 recognizes keyboard inputs of a user, output display, files and directories stored locally on the fixed media drive 908, for example, a hard drive. Different programs, for example, a web browser, an e-mail application, etc., initiated by the user are executed by the operating system with the help of the processor 901, for example, a central processing unit (CPU). The operating system monitors the use of the processor 901.

The image processing application 801a is installed in the computer system 900 and the instructions are stored in the memory unit 902. The panoramic images are transferred from the panoramic imaging machine 200 to the image processing application 801a installed in the computer system 900 of the computing device 801 via the interface 904 or a network. A user initiates the execution of the image processing application 801a by double clicking the icon for the image processing application 801a on the display unit 906 or the execution of the image processing application 801a is automatically initiated on installing the image processing application 801a on the computing device 801. Instructions for constructing a three dimensional tomographic image are retrieved by the processor 901 from the program memory in the form of signals. The locations of the instructions in the modules, for example, 801b, 801c, 801d, 801e, and 801f, are determined by a program counter (PC). The program counter stores a number that identifies the current position in the program of the image processing application 801a.

The instructions fetched by the processor 901 from the program memory after being processed are decoded. The instructions are placed in an instruction register (IR) in the processor 901. After processing and decoding, the processor 901 executes the instructions. For example, the first assignment module 801b defines instructions for assigning a first geometrical attribute set in a first coordinate system to one or more focal troughs 203. The second assignment module 801c defines instructions for assigning a second geometrical attribute set in a second coordinate system to the two dimensional panoramic image. The correlator 801d defines instructions for correlating one or more second geometrical attributes with one or more first geometrical attributes for reconstructing the panoramic image in multiple dimensions. The panoramic image analyzer 801f defines instructions for determining multiple defocused elements of the object along the horizontal dimension of the two dimensional panoramic image. The panoramic image analyzer 801f also defines instructions for determining a transverse dimension for the reconstructed panoramic image by mapping the defocused elements along the horizontal dimension to a translation along the transverse dimension in the first coordinate system on either side of the focal trough 203. The transformation module 801e defines instructions for transforming the multiple dimensions of the reconstructed panoramic image into an orthogonal coordinate system to generate the three dimensional tomographic image of the object, etc., which are stored in the program memory or received from a remote server.

The processor 901 retrieves the instructions defined by the first assignment module 801b, the second assignment module 801c, the correlator 801d, the panoramic image analyzer 801f, and the transformation module 801e, and executes the instructions.

At the time of execution, the instructions stored in the instruction register are examined to determine the operations to be performed. The specified operation is then performed by the processor 901. The operations include arithmetic and logic operations. The operating system performs multiple routines for performing a number of tasks required to assign input devices 907, output devices 910, and memory for execution of the image processing application 801a. The tasks performed by the operating system comprise assigning memory to the image processing application 801a and data, moving data between memory 902 and disk units and handling input/output operations. The operating system performs the tasks on request by the operations and after performing the tasks, the operating system transfers the execution control back to the processor 901. The processor 901 continues the execution to obtain one or more outputs. The outputs of the execution of the image processing application 801a are displayed to the user on the display unit 906.

It will be readily apparent that the various methods and algorithms described herein may be implemented in a computer readable medium appropriately programmed for general purpose computers and computing devices. Typically a processor, for example, one or more microprocessors will receive instructions from a memory or like device, and execute those instructions, thereby performing one or more processes defined by those instructions. Further, programs that implement such methods and algorithms may be stored and transmitted using a variety of media, for example, computer readable media in a number of manners. In one embodiment, hard-wired circuitry or custom hardware may be used in place of, or in combination with, software instructions for implementation of the processes of various embodiments. Thus, embodiments are not limited to any specific combination of hardware and software. A "processor" means any one or more microprocessors, central processing unit (CPU) devices, computing devices, microcontrollers, digital signal processors or like devices. The term "computer readable medium" refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include dynamic random access memory (DRAM), which typically constitutes the main memory. Transmission media include coaxial cables, copper wire and fiber optics, including the wires that comprise a system bus coupled to the processor. Common forms of computer readable media include, for example, a floppy disk, a flexible disk, hard disk, magnetic tape, any other magnetic medium, a compact disc-read only memory (CD-ROM), digital versatile disc (DVD), any other optical medium, punch cards, paper tape, any other physical medium with patterns of holes, a random access memory (RAM), a programmable read only memory (PROM), an erasable programmable read only memory (EPROM), an electrically erasable programmable read only memory (EEPROM), a flash memory, any other memory chip or cartridge, a carrier wave as described hereinafter, or any other medium from which a computer can read. In general, the computer readable programs may be implemented in any programming language. Some examples of languages that can be used include C, C++, C#, Perl, Python, or JAVA. The software programs may be stored on or in one or more mediums as an object code. A computer program product comprising computer executable instructions embodied in a computer readable medium comprises computer parsable codes for the implementation of the processes of various embodiments.

The present invention can be configured to work in a network environment including a computer that is in communication, via a communications network, with one or more devices, for example, one or more imaging machines. The computer may communicate with the devices directly or indirectly, via a wired or wireless medium such as the Internet, Local Area Network (LAN), Wide Area Network (WAN) or Ethernet, Token Ring, or via any appropriate communications means or combination of communications means. Each of the devices may comprise computers, such as those based on the Intel® processors, AMD® processors, UltraSPARC® processors, Sun® processors, IBM® processors, etc. that are adapted to communicate with the computer. Any number and type of machines may be in communication with the computer.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A computer implemented method of constructing a three dimensional tomographic image from a two dimensional panoramic image of an object, comprising:

assigning a set of first geometrical attributes in a first coordinate system to one or more focal troughs, said focal troughs defining curved multidimensional zones relating to predefined focal planes associated with one or more panoramic imaging machines, wherein said set of said first geometrical attributes represents a vertical dimension, a rotational dimension, and a transverse dimension in said first coordinate system;

assigning a set of second geometrical attributes in a second coordinate system to said two dimensional panoramic image of said object, wherein said set of said second geometrical attributes represents a vertical dimension and a horizontal dimension in said second coordinate system;

reconstructing said two dimensional panoramic image in multiple dimensions, wherein said multiple dimensions of said reconstructed panoramic image comprise said vertical dimension of said set of said first geometrical attributes, said rotational dimension of said set of said first geometrical attributes, and a transverse dimension, wherein said reconstruction comprises:

correlating one or more of said second geometrical attributes with one or more of said first geometrical attributes, wherein said vertical dimension of said set of said second geometrical attributes corresponds to said vertical dimension of said set of said first geometrical attributes, and wherein said horizontal dimension of said set of said second geometrical attributes corresponds to said rotational dimension of said set of said first geometrical attributes;

determining, for each of one or more discrete points on said two dimensional panoramic image, a plurality of defocused elements of said object along said horizontal dimension of said two dimensional panoramic image; and determining said transverse dimension for said reconstructed panoramic image by mapping said defocused elements along said horizontal dimension of said two dimensional panoramic image to a translation along said transverse dimension in said first coordinate system on either side of center of said focal troughs; and transforming said multiple dimensions of said reconstructed panoramic image into an orthogonal coordinate system to generate said three dimensional tomographic image of said object.

2. The computer implemented method of claim 1, further comprising determining, for said each of said one or more discrete points on said two dimensional panoramic image, a plurality of defocused elements of said object along said vertical dimension of said two dimensional panoramic image.

3. The computer implemented method of claim 1, wherein said three dimensional tomographic image is generated by an image processing application using said orthogonal coordinate system.

4. The computer implemented method of claim 1, wherein said two dimensional panoramic image is a two dimensional projection of said object developed using said one or more panoramic imaging machines.

5. The computer implemented method of claim 1, wherein said orthogonal coordinate system is a Cartesian coordinate system.

6. The computer implemented method of claim 1, further comprising generating a multi-layered three dimensional image by stacking a plurality of three dimensional tomographic images with thinner focal troughs.

7. The computer implemented method of claim 1, further comprising generating two dimensional cephalometric images using said generated three dimensional tomographic image.

8. The computer implemented method of claim 1, further comprising obtaining a trajectory of center of rotation of an electromagnetic radiation source of said one or more panoramic imaging machines that rotates around said object in said first coordinate system, wherein said trajectory of said center of rotation of said electromagnetic radiation source achieves said predefined focal planes.

9. The computer implemented method of claim 8, further comprising obtaining a measured speed of rotation of said electromagnetic radiation source around said object and a measured speed of rotation of a rotating image film drum of said one or more panoramic imaging machines.

10. A computer implemented system for constructing a three dimensional tomographic image from a two dimensional panoramic image of an object, comprising:

one or more panoramic imaging machines having predefined focal planes;

an image processing application provided on a computing device, said image processing application comprising:

a first assignment module that assigns a set of first geometrical attributes in a first coordinate system to one or more focal troughs, said focal troughs defining curved multidimensional zones relating to said predefined focal planes associated with said one or more panoramic imaging machines, wherein said set of said first geometrical attributes represents a vertical dimension, a rotational dimension, and a transverse dimension in said first coordinate system;

a second assignment module that assigns a set of second geometrical attributes in a second coordinate system to said two dimensional panoramic image of said object, wherein said set of second geometrical attributes represents a vertical dimension and a horizontal dimension in said second coordinate system;

a correlator that correlates one or more of said second geometrical attributes with one or more of said first geometrical attributes for reconstructing said panoramic image in multiple dimensions, wherein said multiple dimensions of said reconstructed panoramic image comprise said vertical dimension of said set of said first geometrical attributes, said rotational dimension of said set of said first geometrical attributes, and a transverse dimension, and wherein said vertical dimension of said set of second geometrical attributes corresponds to said vertical dimension of said set of said first geometrical attributes, and wherein said horizontal dimension of said set of said second geometrical attributes corresponds to said rotational dimension of said set of said first geometrical attributes;

a panoramic image analyzer that determines, for each of one or more discrete points on said two dimensional panoramic image, a plurality of defocused elements of said object along said horizontal dimension of said two dimensional panoramic image;

said panoramic image analyzer that determines said transverse dimension for said reconstructed panoramic image by mapping said defocused elements along said horizontal dimension of said two dimensional panoramic image to a translation along said transverse dimension in said first coordinate system on either side of center of said focal troughs; and a transformation module that transforms said multiple dimensions of said reconstructed panoramic image into an orthogonal coordinate system to generate said three dimensional tomographic image of said object.

11. The computer implemented system of claim 10, wherein said panoramic image analyzer determines, for said each of said one or more discrete points on said two dimensional panoramic image, a plurality of defocused elements of said object along said vertical dimension of said two dimensional panoramic image.

12. The computer implemented system of claim 10, wherein said image processing application generates said three dimensional tomographic image using said orthogonal coordinate system.

13. The computer implemented system of claim 10, wherein said two dimensional panoramic image is a two dimensional projection of said object developed using said one or more panoramic imaging machines.

14. The computer implemented system of claim 10, wherein said image processing application generates a multi-layered three dimensional image by stacking a plurality of three dimensional tomographic images with thinner focal troughs.

15. The computer implemented system of claim 10, wherein said image processing application generates two dimensional cephalometric images using said generated three dimensional tomographic image.

16. The computer implemented system of claim 10, wherein said first assignment module obtains a trajectory of center of rotation of an electromagnetic radiation source of said one or more panoramic imaging machines that rotates around said object in said first coordinate system, wherein said trajectory of said center of rotation of said electromagnetic radiation source achieves said predefined focal planes.

17. The computer implemented system of claim 16, wherein said first assignment module obtains a measured speed of rotation of said electromagnetic radiation source around said object and a measured speed of rotation of a rotating image film drum of said one or more panoramic imaging machines.

18. A computer program product comprising computer executable instructions embodied in a computer readable storage medium, wherein said computer program product comprises:

a first computer parsable program code for assigning a set of first geometrical attributes in a first coordinate system to one or more focal troughs, said focal troughs defining curved multidimensional zones relating to predefined focal planes associated with one or more panoramic imaging machines, wherein said set of said first geometrical attributes represents a vertical dimension, a rotational dimension, and a transverse dimension in said first coordinate system;

a second computer parsable program code for assigning a set of second geometrical attributes in a second coordinate system to a two dimensional panoramic image of an object, wherein said set of said second geometrical attributes represents a vertical dimension and a horizontal dimension in said second coordinate system;

a third computer parsable program code for correlating one or more of said second geometrical attributes with one or more of said first geometrical attributes for reconstructing said panoramic image in multiple dimensions, wherein said multiple dimensions of said reconstructed panoramic image comprise said vertical dimension of said set of said first geometrical attributes, said rotational dimension of said set of said first geometrical attributes, and a transverse dimension, and wherein said vertical dimension of said set of second geometrical attributes corresponds to said vertical dimension of said set of said first geometrical attributes, and wherein said horizontal dimension of said set of said second geometrical attributes corresponds to said rotational dimension of said set of said first geometrical attributes;

a fourth computer parsable program code for determining, for each of one or more discrete points on said two dimensional panoramic image, a plurality of defocused elements of said object along said horizontal dimension of said two dimensional panoramic image;

a fifth computer parsable program code for determining a transverse dimension for said reconstructed panoramic image by mapping said defocused elements along said horizontal dimension of said two dimensional panoramic image to a translation along said transverse dimension in said first coordinate system on either side of center of said focal troughs; and a sixth computer parsable program code for transforming said multiple dimensions of said reconstructed panoramic image into an orthogonal coordinate system to generate said three dimensional tomographic image of said object.

19. The computer program product of claim 18, further comprising a seventh computer parsable program code for determining, for said each of said one or more discrete points on said two dimensional panoramic image, a plurality of defocused elements of said object along said vertical dimension of said two dimensional panoramic image.

20. The computer program product of claim 18, further comprising an eighth computer parsable program code for generating said three dimensional tomographic image using said orthogonal coordinate system.

21. The computer program product of claim 18, further comprising a ninth computer parsable program code for generating a multi-layered three dimensional images by stacking a plurality of three dimensional tomographic images with thinner focal troughs.

* * * * *